United States Patent
Gonzalez et al.

(10) Patent No.: US 6,969,521 B1
(45) Date of Patent: Nov. 29, 2005

(54) AEROSOL INSECT REPELLENT COMPOSITION HAVING LOW VOC CONTENT AND METHOD OF APPLYING SAME TO THE SKIN

(75) Inventors: Anthony D. Gonzalez, Waldwick, NJ (US); Andrew H. Pechko, Ridgewood, NJ (US); Robert E. Kalafsky, Ogdensburg, NJ (US)

(73) Assignee: Avon Products, Inc., New York, NY (US)

( * ) Notice: Subject to any disclaimer, the term of this patent is extended or adjusted under 35 U.S.C. 154(b) by 0 days.

(21) Appl. No.: 09/724,313

(22) Filed: Nov. 28, 2000

(51) Int. Cl.⁷ .............................................. A01N 25/32
(52) U.S. Cl. ................... 424/406; 424/45; 424/47; 424/59; 424/401; 424/720; 514/551; 514/617; 514/738; 514/315; 514/919
(58) Field of Search ................. 424/405, 45, 47, 424/59, 60, DIG. 10, DIG. 13, 406, 401, 424/750; 514/919, 551, 738, 617, 315

(56) References Cited

U.S. PATENT DOCUMENTS

| | | | |
|---|---|---|---|
| 3,159,535 A | 12/1964 | Sesso et al. .................. 167/39 |
| 3,303,091 A * | 2/1967 | Mailander et al. ............ 267/39 |
| 4,047,505 A | 9/1977 | McAndless ................. 119/106 |
| 4,478,853 A | 10/1984 | Chaussee .................... 424/358 |
| 4,695,452 A | 9/1987 | Gannis et al. ................ 424/67 |
| 4,883,659 A | 11/1989 | Goodman et al. ............ 424/78 |
| 4,913,897 A | 4/1990 | Chvapil et al. ............... 424/59 |
| 4,970,220 A * | 11/1990 | Chaussee .................... 514/358 |
| 4,981,689 A | 1/1991 | Shikinami et al. .......... 424/409 |
| 5,039,516 A | 8/1991 | Goodman et al. ............ 424/59 |
| 5,055,299 A * | 10/1991 | Dohara et al. .............. 424/405 |
| 5,102,662 A | 4/1992 | Gallagher ................... 424/409 |
| 5,143,900 A | 9/1992 | Steltenkamp et al. ......... 512/26 |
| 5,145,604 A | 9/1992 | Neumiller ................... 252/312 |
| 5,196,200 A | 3/1993 | Wilson et al. .............. 424/411 |
| 5,401,870 A | 3/1995 | Raleigh et al. ............. 556/445 |
| 5,531,993 A | 7/1996 | Griat .......................... 424/401 |
| 5,565,208 A * | 10/1996 | Vlasblom .................... 424/405 |
| 5,804,203 A | 9/1998 | Hahn et al. ................. 424/401 |
| 5,855,903 A | 1/1999 | Warren et al. .............. 424/405 |
| 5,863,545 A | 1/1999 | Griat .......................... 424/401 |
| 5,916,541 A * | 6/1999 | Stewart ....................... 424/59 |
| 5,932,194 A | 8/1999 | Plessix et al. ................ 424/59 |
| 5,980,871 A | 11/1999 | Lukenbach et al. ........... 424/59 |
| 5,989,529 A | 11/1999 | Kaplan ........................ 424/59 |
| 6,001,379 A | 12/1999 | Griat .......................... 424/401 |
| 6,030,629 A | 2/2000 | Hansenne ................... 424/401 |
| 6,306,905 B1 * | 10/2001 | Kurz et al. | |

FOREIGN PATENT DOCUMENTS

| | | |
|---|---|---|
| GB | 1 445 813 | 8/1976 |
| WO | WO 92/04419 | 3/1992 |
| WO | WO 96/20691 | 7/1996 |
| WO | WO 9622686 | 8/1996 |

OTHER PUBLICATIONS

Hawley, Condnsed Chemical Dictionary—emulsion, p340, 1977.*

Supplementary European Search Report dated Mar. 27, 2003, in corresponding to EP 01998220.

* cited by examiner

*Primary Examiner*—Neil S. Levy
(74) *Attorney, Agent, or Firm*—Ohlandt, Greeley, Ruggiero & Perle, L.L.P.

(57) ABSTRACT

Disclosed is an aerosol insect repellent composition. The composition has (a) an amount of an insect repellent effective to repel insects when applied to the skin and (b) a cosmetically-acceptable vehicle in which to disperse and deliver the insect repellent active. The vehicle has (i) a VOC component capable of volatilizing upon exposure to a reduction in pressure for delivering the composition in an aerosol form, and (ii) a non-VOC component. The aerosol composition has a VOC content of not greater than about 55 wt. % based upon the weight of the aerosol composition. Further disclosed is a method of repelling insects from skin wherein the aerosol composition is applied to or sprayed on the skin.

41 Claims, No Drawings

AEROSOL INSECT REPELLENT COMPOSITION HAVING LOW VOC CONTENT AND METHOD OF APPLYING SAME TO THE SKIN

BACKGROUND OF THE INVENTION

1. Field of the Invention

The present invention relates to an aerosol insect repellent composition. More particularly, the present invention relates to such a composition having a low level of volatile organic compounds.

2. Description of the Prior Art

Insect repellent compositions are available commercially in aerosol form. Consumers find aerosol compositions easy to administer to both the skin and to clothing. Further, aerosol compositions help consumers avoid the inconvenience of having to apply and spread the insect repellent with the hands.

An environmental concern with prior art aerosol insect repellent compositions is the high level of volatile organic compound (VOC) components present. Commercially available aerosol compositions typically range in VOC content from about 60 percentage by weight (wt. %) to about 90 wt. %. VOC components commonly employed in aerosol compositions include low molecular weight hydrocarbons and alcohols. VOC components may also serve as solvents and/or propellants in aerosolized insect repellent compositions. Due to increased environmental scrutiny of VOC components, it would be a desirable achievement to effectively reduce the VOC content in aerosol compositions and, particularly, topically applied insect repellent compositions, without deleteriously affecting the efficacy or dispensability of such compositions.

To reduce the VOC content in an aerosol insect repellent composition is difficult due to formulation considerations. Frequently, reducing the VOC content requires introducing or increasing the content of water in the aerosol composition. Most insect repellents or actives are insoluble in water. Thus, the actives may become more difficult to disperse, solubilize and/or stabilize. Further, the increased water content may increase the risk of corrosion of metal (e.g., aluminum and tin) dispensing canisters.

SUMMARY OF THE INVENTION

It is an object of the present invention to provide an aerosol insect repellent composition having a low VOC content.

It is another object of the present invention to provide such an aerosol insect repellent composition that minimizes the corrosion of metal dispensing containers that may occur when VOC components are replaced.

It is a further object of the present invention to provide such an aerosol insect repellent composition that does not interfere with consistency of spray delivery.

These and other objects and advantages of the present invention are achieved by an aerosol insect repellent having an amount of an insect repellent active effective to repel insects when applied to the skin and a cosmetically-acceptable vehicle in which to disperse and deliver the insect repellent active. The vehicle has (i) a VOC component, which may be capable of volatilizing upon exposure to a reduction in pressure to deliver the composition in an aerosol form, and (ii) a non-VOC component. The aerosol composition has a VOC content no greater than about 55 wt. % based on the total weight of the composition.

The present invention also provides an environmentally preferred method of repelling insects from the skin. The method includes applying the above aerosol composition to the skin.

DETAILED DESCRIPTION OF THE INVENTION

In the present invention, it was unexpectedly and surprisingly found that an aerosol insect repellent composition could be formulated having a low VOC content. VOC content is defined herein as the percent by weight of the VOC component in the composition. A VOC is any compound of carbon, excluding carbon monoxide, carbon dioxide, metallic carbides or carbonates, and ammonium carbonate, which participates in atmospheric photochemical reactions. This definition includes any such organic compound other than those that have been determined to have negligible photochemical reactivity as listed in 40 CFR 51.100(s), which is incorporated herein by reference.

The aerosol composition can be formulated to neither cause significant corrosion of metal dispensing containers or canisters nor interfere with consistency of spray delivery. The aerosol composition can also be formulated to impart a desirable feel and appearance to the skin.

In accordance with the present invention, the VOC content of a conventional aerosol composition can be regulated by partially substituting one or more non-volatile organic compound (non-VOC) components for the VOC component. In particular, the non-VOC component can partially or completely substitute for ethanol or other alcohols that are VOC solvents and commonly used in aerosolized insect repellent compositions. Further, the addition of non-VOC components surprisingly permits a reduction in the amount of VOC propellants, such as hydrocarbons that are commonly employed in aerosol compositions.

The aerosol composition of the present invention has a VOC content about 1 wt. % to about 55 wt. % based on the total weight of the composition. Preferably, the composition has a VOC content about 1 wt. % to about 45 wt. %, and most preferably about 1 wt. % to about 35 wt. %, based on the total weight of the composition.

The present invention has one or more non-VOC components. The non-VOC components useful in the present aerosol composition include those that are compatible and miscible with the insect repellent active and the propellant.

The non-VOC component is preferably in liquid or fluid form. The non-VOC components have a vapor pressure less than or equal to about 0.1 mHg at 20° C., or have 12 or more carbon atoms. The non-VOC components that can be used in the present composition include, but are not limited to, polyols, such as butylene glycol, ethylene glycol, propylene glycol and hexylene glycol; vegetable oils; esters such as octyl palmitate, isopropyl myristate, and isopropyl palmitate; non-volatile ethers such as dicapryl ether and dimethyl isosorbide; fatty alcohols such a cetyl alcohol, stearyl alcohol, and behenyl alcohol; silicone oils such as dimethicones and polysiloxanes; and non-volatile hydrocarbon oils such as mineral oil, petrolatum, isoeicosane and polyisobutene.

The non-VOC components are present in the aerosol composition at up to about 50 wt. % based on the total weight of the composition. Preferably, the non-VOC components are present in the aerosol composition at about 5 wt. % to about 30 wt. % based on the total weight of the composition.

In a preferred embodiment, the non-VOC component may also comprise water. The use of water is desired to partially replace VOC components in the composition, but has been commercially impractical because of the corrosive effect of water on the aerosol canister. The present aerosol composition has achieved a proper balance. Thus, the present composition may have water in an amount up to about 50 wt. %, preferably about 5 wt. % to about 40 wt. %, and most preferably about 10 wt. % to about 30 wt. %, based on the total weight of the composition. If there is water and/or a low molecular weight alcohol in the composition, any additional ingredients included in the non-VOC component shall likewise be compatible therewith.

The insect repellent or active employed in the present composition may be one or more insect repellents known in the art. Typically, the insect repellent or active will be an oil-soluble compound that dissolves in the oil phase of the aerosol composition. Such insect repellents or actives include, but are not limited to, N,N diethyl-m-toluamide (DEET), ethyl butylacetylaminopropionate (IR3535 by Merck Co.), hydroxyethyl isobutyl piperidine carboxylate (1-piperidinecarboxylic acid) (Bayer KBR 3023), oil of citronella, soy bean oil, lemon grass oil, geranium/geraniol oil, and p-menthane-3,8-diol. Other useful actives are disclosed in U.S. Pat. Nos. 5,130,136 and 5,698,209, which are incorporated herein by reference. The preferred insect repellent actives are DEET, IR3535, Bayer KBR 3023, p-menthane-3,8-diol, and oil of citronella.

The insect repellent is present in an amount effective to repel insects. The insect repellent is preferably present at up to about 50 wt. %, and more preferably about 0.5 wt. % to about 45 wt. % based on the total weight of the composition.

The VOC component of the present aerosol composition may comprise a volatile propellant. Suitable propellants are those that can be compressed or liquefied within a dispensing spray canister, yet expand or volatilize to vapor or gas form upon exposure to ambient temperature and pressure conditions to deliver the composition in an aerosol form. Suitable propellants include hydrocarbons having 1 to 5 carbon atoms. Representative propellants include, but are not limited to, methane, ethane, propane, isopropane, butane, isobutane, butene, pentane, isopentane, neopentane, pentene, hydrofluorocarbons (HFC), chlorofluorocarbons (CFC), dimethyl ether, and mixtures of the foregoing. Preferred propellants include propane, isopropane, isobutane, and butane. In addition to functioning as a propellant, volatile hydrocarbons may act as solvents and/or solubilizers of the insect repellent active.

The propellant concentration is up to about 30 wt. %, preferably about 1 wt. % to about 25 wt. %, and more preferably about 5 wt % to about 20 wt. %, based on the total weight of the aerosol composition.

The present aerosol composition optionally has one or more VOC low molecular weight alcohols or diols each having from 1 to 8 carbon atoms. Such alcohols assist in the solubilization and dispersion of the insect repellent active and the compatibilization of water in the aerosol composition. The alcohols also assist in maintaining the solubilization and/or dispersion of the insect repellent active as the propellant is progressively expended from the dispensing canister through spraying.

Such suitable alcohols include, but are not limited to, methanol, ethanol, propanol, isopropanol, butanol, isobutanol, pentanol, hexanol, heptanol, octanol, and mixtures thereof. Ethanol is preferred due to its low cost and ability to solubilize efficiently most insect repellents actives.

If present, the alcohol is up to about 45 wt. %, preferably about 1 wt. % to about 40 wt. %, and more preferably about 5 wt. % to about 30 wt. %, of the total weight of the aerosol composition.

A preferred aerosol composition has about 0.5 wt. % to about 45 wt. % of the insect repellent active, about 5 wt. % to about 20 wt. % of the propellant, about 5 wt. % to about 30 wt. % of the alcohol, about 5 wt. % to about 40 wt. % water, and about 5 wt. % to about 30 wt. % of a non-VOC component other than water, based on the total weight of the composition.

Optionally, the present aerosol composition may have a sunscreen. Such sunscreens or sunscreen actives include those for UVA and UVB protection (290 to 400 nanometer solar radiation). The sunscreen may be any organic or inorganic compound known in the art. These compounds include, but are not limited to, oxybenzone, sulisobenzone, dioxybenzone, menthyl antranilate, para aminobenzoic acid (PABA), octyl methoxycinnamate, octocrylene, drometrizole trisiloxane, octyl salicylate, homomenthyl salicylate, octyl dimethyl PABA, TEA salicylate, titanium dioxide, zinc oxide, butylmethoxy dibenzoylmethane, 4-methyl benzilidene camphor, octyl triazone, terephthalydiene dicamphor sulfonic acid, ethyl PABA, hydroxy methylphenyl benzotriazole, methylene bis-benzotriazoyltetramethylbutylphenol, bis-ethylhexyloxyphenol methoxyphenol triazine, and mixtures of the foregoing. Other useful sunscreen actives include those disclosed in U.S. Pat. No. 5,000,937, which is incorporated herein.

If present, sunscreens will be in an amount from about 1 wt. % to about 35 wt. %, based on the total weight of the composition.

Also optionally, the present aerosol composition may have a film former. The film former will improve water, sweat and wear resistance. The film former leaves a film residue on the surface of the skin either immediately or upon evaporation of volatiles in the composition. The film former can also enhance the spread characteristics of the composition, which allows the composition to be more uniformly and consistently applied to the skin. The film former can also help maintain the insect repellent at the surface of the skin for a longer period of time than it would otherwise remain without the film former. The film former can also afford sustained release of the insect repellent.

The amount of film former employed will vary depending on desired film residue thickness and chemical properties. However, the typical amount of film former in the present composition ranges from about 0.1 wt. % to about 20 wt. % based on the total weight of the composition.

The film former may be water-soluble, oil-soluble or both. The film-formers that can be used in the present invention include waxes, such as beeswax (synthetic or natural) and botanical waxes; acrylate copolymers such as acrylate/octylacrylamide copolymers and acrylate/vinyl acetate copolymers; cellulosic polymers such as methyl cellulose and hydroxyethyl cellulose; ethylene/acrylic acid copolymer; polyacrylic acid; $C_1$ to $C_5$ alkyl galactomannan; isododecane/ethylene mixed copolymer; adipic acid/diethylene glycol/glycerin crosspolymer; trimethylpentanediol/adipic acid copolymer; trimethylpentanediol/adipic acid/isononanoic acid; PVP/hexadecene copolymer (e.g., Ganex V-216); PVP/eicosene copolymer (e.g., Ganex V-220); alpha olefin/isopropyl maleate/MA polymer; cycloalkyl methacrylate copolymer/isododecane; trimethyl polysiloxane octadecene/MA copolymer; PPG-12/SMDI copolymer; acrylates $C_{10}$ to $C_{30}$ alkyl acrylate crosspolymer; cetyl hydroxyethylcellulose; dimethiconol; dimethicone; diglycol/cyclohexanedimethanol/isophthalates/sulfoisophthalate copolymer; polyethylene; and polyurethane resins. The polyurethane resins include Polyurethane-1, Polyurethane-2, Polyurethane-4, Polyurethane-5, and mixtures thereof. These polyurethane resins are described in the International Cosmetic Ingredient Dictionary and Handbook, 8$^{th}$ edition, Printed Edition Pages 1152–1153, which is incorporated herein by reference. Additional film formers include those set forth in U.S. Pat. No. 5,916,541, which is incorporated herein by reference.

Further optionally, the present composition may have one or more of the following additional ingredients: anesthetics, anti-allergenics, antibacterials, antifungals, anti-inflammatories, antiseptics, chelating agents, colorants, depigmenting agents, emulsifiers, emollients, exfolients, fragrances, humectants, lubricants, moisturizers, pharmaceutical agents, preservatives, skin penetration enhancers, skin protectants, stabilizers, surfactants, thickeners, viscosity modifiers, and vitamins.

Depending upon the formulation, the aerosol composition may take the form of a solution, a suspension or an emulsion. Emulsions may be either oil-in-water or water-in-oil. Regardless of form, the composition must be thin enough at the time of dispensing or of sufficiently low viscosity to be sprayed from an aerosol dispensing canister. Typically, the composition is forced through a small orifice due to a pressure differential between the interior of the canister and the ambient environment.

EXAMPLE 1

| Component | wt. % |
|---|---|
| Ethanol | 45 |
| Propane | 10 |
| Ethyl butylacetylaminoproprionate | 20 |
| Hexylene glycol | 10 |
| Water | 15 |

EXAMPLE 2

| Component | wt. % |
|---|---|
| Ethanol | 20 |
| Propane | 6 |
| Isopropane | 4 |
| p-Methane diol | 20 |
| Buylene glycol | 50 |

EXAMPLE 3

| Component | wt. % |
|---|---|
| N,N Diethyltoluamide (DEET) | 50 |
| Isopropyl myristate | 10 |
| Octyldodecanol | 5 |
| Dimethyl ether | 5 |
| Isopropanol | 30 |

EXAMPLE 4

| Component | wt. % |
|---|---|
| Geraniol | 5 |
| Oil of Citronella | 10 |
| Propylene glycol | 25 |
| PPG-12/SMDI copolymer | 5 |
| Isododecane | 20 |
| Dioctyl ether | 30 |
| Butane | 5 |

EXAMPLE 5

| Component | wt. % |
|---|---|
| Ethanol | 20 |
| Propane | 6 |
| Isopropane | 4 |
| p-Menthane diol | 20 |
| Soybean oil | 5 |
| Isopropyl palmitate | 25 |
| Water | 20 |

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. An insect repellent composition dispensable from an aerosol container, comprising:

from about 0.5 to about 50 wt. % of an insect repellent effective to repel insects when applied to the skin, wherein said insect repellant is selected from the group consisting of N,N-diethyl-m-toluamide, ethyl butylacetylaminopropionate, hydroxyethyl isobutyl piperidine carboxylate, oil of citronella, soy bean oil, lemon grass oil, geranium/geraniol oil, and p-menthane-3,8-diol;

one or more film formers, the one or more film formers being present at about 0.1 wt. % to about 10 wt. %; and a cosmetically-acceptable aerosol vehicle to disperse and deliver the insect repellent active, the vehicle having (i) a volatile organic compound (VOC) component, the VOC component having from about 1 to about 30 wt. % of a propellant and from about 1 to about 45 wt. % of an alcohol of 1 to 8 carbon atoms; and (ii) a non-volatile organic compound (non-VOC) component having water in an amount up to about 50 wt. %, wherein the VOC component is not greater than about 55 wt. %, wherein the composition takes a form selected from the group consisting of a solution, a suspension, and a dispersion, wherein the composition is applied to humans, and wherein all percentages are based on the total weight of the composition.

2. The composition of claim 1, wherein the VOC component is about 1 wt. % to about 45 wt. % based on the total weight of the composition.

3. The composition of claim 1, wherein the VOC component is about 1 wt. % to about 35 wt. % based on the total weight of the composition.

4. The composition of claim 1, wherein the propellant is present at about 5 wt. % to about 20 wt. % based on the total weight of the composition.

5. The composition of claim 1, wherein the insect repellent is present at about 0.5 wt. % to about 45 wt. % based on the total weight of the composition.

6. The composition of claim 1, wherein the non-VOC component is present at up to about 50 wt. % based on the total weight of the composition.

7. The composition of claim 6, wherein the non-VOC component is present at about 5 wt. % to about 30 wt. % based on the total weight of the composition.

8. The composition of claim 1, wherein the non-VOC component has a compound selected from the group consisting of polyols, vegetable oils, esters, ethers, fatty alcohols, silicone oils, hydrocarbon oils, water, and any mixtures thereof.

9. The composition of claim 1, wherein the composition is a solution.

10. The composition of claim 1, wherein the water is present in an amount about 5 wt. % to about 40 wt. % based on the total weight of the composition.

11. The composition of claim 1, wherein the water is present in an amount about 10 wt. % to about 30 wt. % based on the total weight of the composition.

12. The composition of claim 1, wherein the alcohol has 1 to 8 carbon atoms in an amount about 1 wt. % to about 40 wt. % based on the total weight of the composition.

13. The composition of claim 1, wherein the composition is a suspension.

14. The composition of claim 1, further comprising a sunscreen in an amount about 1 wt. % to about 35 wt. %, based on the total weight of the composition.

15. The composition of claim 12, wherein said alcohol is selected from the group consisting of methanol, ethanol, propanol, isopropanol, butanol, isobutanol, pentanol, hexanol, heptanol, octanol, and any mixtures thereof.

16. The composition of claim 15, wherein said alcohol is selected from the group consisting of ethanol, propanol, isopropanol, butanol, isobutanol, and any mixtures thereof.

17. An insect repellent composition dispensable from an aerosol container, comprising:
from about 0.5 wt. % to about 45 wt. % of an insect repellent effective to repel insects when applied to the skin, wherein said insect repellant is selected from the group consisting of N,N-diethyl-m-toluamide, ethyl butylacetylaminopropionate, hydroxyethyl isobutyl piperidine carboxylate, oil of citronella, soy bean oil, lemon grass oil, geranium/geraniol oil, and p-menthane-3,8-diol; and
a cosmetically-acceptable aerosol vehicle to disperse and deliver the insect repellent active, the vehicle having
  (i) a volatile organic compound (VOC) component, the VOC component having from about 1 to about 30 wt. % of a propellant and from about 1 to about 45 wt. % of an alcohol of 1 to 8 carbon atoms; and
  (ii) a non-volatile organic compound (non-VOC) component of water in an amount about 5 wt. % to about 30 wt. % and a non-VOC component other than water in an amount about 5 wt. % to about 30 wt. %,
wherein the VOC component is present in an amount about 1 wt. % to about 55 wt. %, wherein the composition takes a form selected from the group consisting of a solution, a suspension, and a dispersion, wherein the composition is applied to humans, and wherein all percentages are based on the total weight of the composition.

18. The composition of claim 17, wherein the propellant is present at about 1 wt. % to about 25 wt. % based on the total weight of the composition.

19. The composition of claim 18, wherein the alcohol having 1 to 8 carbon atoms is present at about 5 wt. % to about 30 wt. %.

20. A method of repelling insects from skin comprising spraying on the skin an aerosol composition having:
from about 0.5 to about 50 wt. % of an insect repellent effective to repel insects when applied to the skin, wherein said insect repellant is selected from the group consisting of N,N-diethyl-m-toluamide, ethyl butylacetylaminopropionate, hydroxyethyl isobutyl piperidine carboxylate, oil of citronella, soy bean oil, lemon grass oil, geranium/geraniol oil, and p-menthane-3,8-diol; and
a cosmetically-acceptable aerosol vehicle to disperse and deliver the insect repellent active, the vehicle having
  (i) a volatile organic compound (VOC) component, the VOC component having from about 1 to about 30 wt. % of a propellant and from about 1 to about 45 wt. % of an alcohol of 1 to 8 carbon atoms; and
  (ii) a non-volatile organic compound (non-VOC) component having water in an amount about 5 wt. % to about 40 wt. %,
wherein the VOC component is not greater than about 55 wt. %, wherein the composition takes a form selected from the group consisting of a solution, a suspension, and a dispersion, wherein the composition is applied to humans, and wherein all percentages are based on the total weight of the composition.

21. The method of claim 20, wherein the VOC component is about 1 wt. % to about 45 wt. % based on the total weight of the composition.

22. The method of claim 20, wherein the insect repellent is present in an amount about 0.5 wt. % to about 45 wt. % based on the total weight of the composition, and wherein the non-VOC component is present in an amount up to 50 wt. % based on the total weight of the composition.

23. The composition of claim 4, wherein said propellant is selected form the group consisting of methane, ethane, propane, isopropane, butane, isobutane, butene, pentane, isopentane, neopentane, pentene, hydrofluorocarbons, chlorofluorocarbons, dimethyl ether, and any mixtures thereof.

24. The composition of claim 19, wherein said alcohol is selected from the group consisting of ethanol, propanol, isopropanol, butanol, isobutanol, and any mixtures thereof.

25. The composition of claim 20, further comprising a film former.

26. The composition of claim 17, further comprising a film former.

27. An insect repellent composition dispensable from an aerosol container, comprising:
from about 0.5 to about 50 wt. % of an insect repellent effective to repel insects when applied to the skin, wherein said insect repellant is selected from the group consisting of N,N-diethyl-m-toluamide, ethyl butylacetylaminopropionate, hydroxyethyl isobutyl piperidine carboxylate, oil of citronella, soy bean oil, lemon grass oil, geranium/geraniol oil, and p-menthane-3,8-diol; and
a cosmetically-acceptable aerosol vehicle to disperse and deliver the insect repellent active, the vehicle having (i) a volatile organic compound (VOC) component, the VOC component having from about 1 to about 30 wt. % of a propellant and from about 1 to about 45 wt. % of an alcohol of 1 to 8 carbon atoms; and (ii) a non-volatile organic compound (non-VOC) component having water in an amount up to about 50 wt. %, wherein the VOC component is not greater than about 55 wt. %, wherein the composition takes a form of a dispersion, wherein the composition is applied to humans, and wherein all percentages are based on the total weight of the composition.

28. The method of claim 20, wherein the composition is a dispersion.

29. The composition of claim 17, wherein the composition is a suspension.

30. The composition of claim 17, wherein the composition is a dispersion.

31. A method of repelling insects from skin, comprising spraying on the skin an aerosol composition having:

from about 0.5 to about 50 wt. % of an insect repellent effective to repel insects when applied to the skin, wherein said insect repellant is selected from the group consisting of N,N-diethyl-m-toluamide, ethyl butylacetylaminopropionate, hydroxyethyl isobutyl piperidine carboxylate, oil of citronella, soy bean oil, lemon grass oil, geranium/geraniol oil, and p-menthane-3,8-diol; and a cosmetically-acceptable aerosol vehicle to disperse and deliver the insect repellent active, the vehicle having (i) a volatile organic compound (VOC) component, the VOC component having from about 1 to about 30 wt. % of a propellant and from about 1 to about 45 wt. % of an alcohol of 1 to 8 carbon atoms; and (ii) a non-volatile organic compound (non-VOC) component having water in an amount up to about 50 wt. %, wherein the VOC component is not greater than about 55 wt. %, wherein the composition takes a form of a solution, wherein the composition is applied to humans, and wherein all percentages are based on the total weight of the composition.

32. A method of repelling insects from skin, comprising spraying on the skin an aerosol composition having:

from about 0.5 to about 50 wt. % of an insect repellent effective to repel insects when applied to the skin, wherein said insect repellant is selected from the group consisting of N,N-diethyl-m-toluamide, ethyl butylacetylaminopropionate, hydroxyethyl isobutyl piperidine carboxylate, oil of citronella, soy bean oil, lemon grass oil, geranium/geraniol oil, and p-menthane-3,8-diol; and a cosmetically-acceptable aerosol vehicle to disperse and deliver the insect repellent active, the vehicle having (i) a volatile organic compound (VOC) component, the VOC component having from about 1 to about 30 wt. % of a propellant and from about 1 to about 45 wt. % of an alcohol of 1 to 8 carbon atoms; and (ii) a non-volatile organic compound (non-VOC) component having water in an amount up to about 50 wt. %, wherein the VOC component is not greater than about 55 wt. %, wherein the composition takes a form of a suspension, wherein the composition is applied to humans, and wherein all percentages are based on the total weight of the composition.

33. The composition of claim 5, wherein said insect repellent is selected from the group consisting of N,N diethyl-m-toluamide, ethyl butylacetylaminopropionate, hydroxyethyl isobutyl piperidine carboxylate (1-piperidinecarboxylic acid), oil of citronella, p-menthane-3,8-diol, and any mixtures thereof.

34. The composition of claim 5, wherein said insect repellent is p-methane-3,8-diol.

35. The composition of claim 5, wherein said insect repellent is N,N diethyl-m-toluamide.

36. The composition of claim 5, wherein said insect repellent is ethyl butylacetylaminopropionate.

37. The composition of claim 5, wherein said insect repellent is hydroxyethyl isobutyl piperidine carboxylate.

38. The composition of claim 5, wherein said insect repellent is oil of citronella.

39. The composition of claim 5, wherein said insect repellent is soybean oil.

40. The composition of claim 5, wherein said insect repellent is lemon grass oil.

41. The composition of claim 5, wherein said insect repellent is geranium/geraniol oil.

* * * * *